United States Patent [19]

Lysenko

[11] Patent Number: 5,021,580

[45] Date of Patent: Jun. 4, 1991

[54] POLYBENZOXAZOLES HAVING PENDANT METHYL GROUPS

[75] Inventor: Zenon Lysenko, Midland, Mich.

[73] Assignee: The Dow Chemical Company, Midland, Mich.

[21] Appl. No.: 425,159

[22] Filed: Oct. 23, 1989

[51] Int. Cl.$^5$ .................. C07D 211/72; C07D 213/00; C07C 205/00
[52] U.S. Cl. .................................... 546/307; 528/183; 546/1; 564/360; 568/706
[58] Field of Search .................... 528/183; 546/1, 307; 564/360; 568/706

[56] References Cited

U.S. PATENT DOCUMENTS

| | | | |
|---|---|---|---|
| 3,509,108 | 4/1970 | Prince | 528/342 |
| 3,671,491 | 6/1972 | Loft et al. | 528/210 |
| 3,943,125 | 3/1976 | Gerber | 546/307 |
| 4,108,835 | 8/1978 | Arnold et al. | 528/183 |
| 4,606,875 | 8/1986 | Chenevey et al. | 264/85 |
| 4,864,010 | 9/1989 | Schrock et al. | 528/185 |
| 4,912,246 | 3/1990 | Lysenko et al. | 528/706 |

FOREIGN PATENT DOCUMENTS 0312931  4/1989  European Pat. Off. .

OTHER PUBLICATIONS

Lysenko et al., *Process for the Preparation of Amino-1,-3-Benzenediol*, Ser. No. 290,068 (filed Dec. 27, 1988).
Lysenko et al., *Process for the Preparation of Amino-1,-3-Benzenediol*, Ser. No. 506,406 (filed Apr. 6, 1990).
Tsai et al., "Benzobisazole Rigid-Rod Polymers with Pendant Methyl Groups", 29 *Polymer Preprints* 324 (1988).
Chauh et al., "Cross-Linked Benzobisthiazole Rigid-Rod Polymers vai Labile Methyl Groups", 60 *Polymer Materials: Science & Engineering*, 517 (1989).
Arnold, "Structural Modification of Rigid-Rod Polymers", *The Materials Science and Engineering of Rigid-Rod Polymers* at 117 (Materials Research Society 1989).

*Primary Examiner*—Harold D. Anderson
*Assistant Examiner*—Terressa M. Mosley

[57] ABSTRACT

Polybenzoxazole polymers can be synthesized from BB-monomer having pendant methyl groups. The resulting polymer has pendant methyl groups, which can be used to cross-link the polymers.

6 Claims, No Drawings

POLYBENZOXAZOLES HAVING PENDANT METHYL GROUPS

STATEMENT OF GOVERNMENT INTEREST

This invention was made with government support under Contract F33615-85-C-5113 awarded by the Department of the Air Force. The government has certain rights in this invention.

BACKGROUND OF THE INVENTION

This invention relates to the art of polybenzoxazole (PBO) polymers.

Polybenzoxazoles are a class of polymers within the larger class of polybenzazoles. Polybenzazoles (PBZ) are generally classified as AB-polymers, containing a plurality of mer units depicted in formula 1(a), or AA/BB, containing a plurality of mer units which conform with formula 1(b)

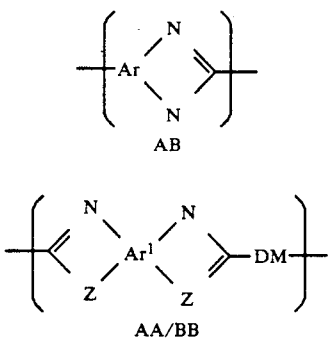

wherein:
each Ar is an aromatic group,
DM is a divalent organic moiety which is and inert in acid under polymerization conditions,
each Z is either —O—, —S— or —NR—, wherein R is a hydrogen atom or an aromatic moiety which is stable under PBZ synthesis and processing conditions and does not interfere with the synthesis or later use of the polymer.

(For the purpose of this application, when the nitrogen atoms and Z moieties of a mer unit are depicted as bonded to an aromatic group without indicating their position, as in Formulae 1(a)–(b), it shall be understood that:

(1) nitrogen atoms and Z moieties in an azole ring are bonded to the aromatic group in ortho position with respect to each other; and (2) if the mer unit contains two azole rings, one nitrogen atom and Z moiety may be in either cis-position or trans-position with respect to the other nitrogen atom and Z moiety, as described and illustrated in 11 Ency. Poly. Sci. & Eng., supra, at 602, which is incorporated herein by reference.)

In polybenzoxazole polymers, each Z group is an oxygen atom.

Polybenzazoles are synthesized by the reaction of one or more difunctional monomers, each of which contains at least two functional moieties chosen from the group consisting of electron-deficient carbon groups and o-amino-basic moieties. Such reactions are illustrated in formulae 2(a) and (b).

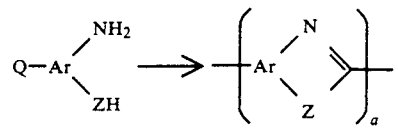

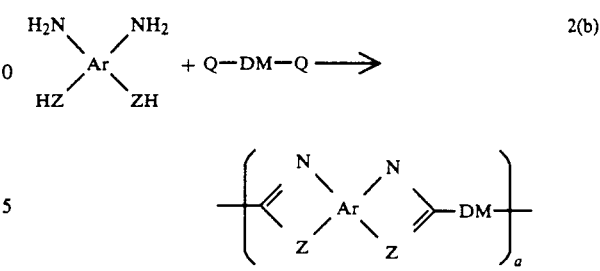

wherein each Q is an electron-deficient carbon group and all other moieties have the meaning and preferred embodiments previously given. The divalent organic moiety DM ordinarily comprises an aromatic group.

Polybenzazole polymers, their properties and their synthesis are discussed in detail in the following references: Sybert et al., *Liquid Crystalline Polymer Compositions, Process and Products*, U.S. Pat. No. 4,772,678 (Sept. 20, 1988): Wolfe et al., *Liquid Crystalline Polymer Compositions, Process and Products*, U.S. Pat. No. 4,703,103 (Oct. 27, 1987): Wolfe et al., *Liquid Crystalline Polymer Compositions, Process and Products*, U.S. Pat. No. 4,533,692 (Aug. 6, 1985): Wolfe et al., *Liquid Crystalline Poly(2,6-Benzothiazole) Compositions, Process and Products*, U.S. Pat. No. 4,533,724 (Aug. 6, 1985); Wolfe, *Liquid Crystalline Polymer Compositions, Process and Products*, U.S. Pat. No. 4,533,693 (Aug. 6, 1985): Imai et al. "Polybenzoxazoles and Polybenzothiazoles," 83 Makromol. Chem. 167 (1965), Evers, *Thermoxadatively Stable Articulated p-Benzobisoxazole and p-Benzobisthiazole Polymers*, U.S. Pat. No. 4,359,567 (Nov. 16, 1982); Tsai et al., *Method for Making Heterocyclic Block Copolymer*, U.S. Pat. No. 4,578,432 (Mar. 25, 1986) and 11 Ency. Poly. Sci. & Eng., *Polybenzothiazoles and Polybenzoxazoles*, 601 (J. Wiley & Sons 1988), which are incorporated herein by reference.

Polybenzazoles are soluble in strong acids. However, they are substantially unreactive, and do not provide reactive sites to permit modification of the polymer properties, such as cross-linking to decrease solubility in acids. What are needed are monomers and polybenzoxazole polymers or copolymers which provide reactive sites.

SUMMARY OF THE INVENTION

One aspect of the present invention is a BB-PBO monomer comprising:
(a) an aromatic group;
(b) two o-amino-hydroxy moieties bonded to the aromatic group; and
(c) a methyl group bonded to the aromatic group.

A second aspect of the present invention is a polybenzazole polymer or copolymer having a plurality of mer units, wherein at least one mer unit comprises:
(a) a first aromatic group;
(b) two oxazole rings fused with the first aromatic group;
(c) a methyl group bonded to the first aromatic group; and (d) a divalent organic moiety which is stable and inert under polybenzoxazole polymerizing conditions bonded to one of the azole rings.

A third aspect of the present invention is a cross-linked polybenzazole polymer comprising a plurality of polybenzazole polymer chains linked by cross-linking moieties, which contain one or more methylene moieties bonded to aromatic groups which are fused with two oxazole moieties within the polybenzazole chain.

Monomers of the present invention can be used to form polymers of the present invention containing pendant methyl groups. Those pendant methyl groups can be used to promote cross-linking to improve resistance to dissolution by acid.

Detailed Description of the Invention

Definitions

The following terms are used repeatedly throughout this application, and have the meaning and preferred embodiments defined herein unless otherwise specified.

AA-Monomer—A monomer suitable for synthesizing polybenzazole polymers, comprising two electron-deficient carbon groups linked by a divalent organic moiety (DM) which is inert with respect to all reagents under polybenzoxazole polymerization conditions. The electron-deficient carbon groups have the definition and preferred embodiments given herein. The divalent organic moiety is preferably alkyl or an aromatic group, as herein defined, is more preferably an aromatic group, and is most preferably a six-membered aromatic group. Examples of suitable AA-monomers and references to their synthesis are provided in U.S. Pat. No. 4,533,693 at columns 25–32, Tables 4–6, which is incorporated herein by reference. Preferred examples of AA-monomers include terephthalic acid, isophthalic acid, bis-(4-benzoic) acid and oxy-bis-(4-benzoic acid) and acid halides thereof.

AB-Monomer—A monomer suitable for synthesizing polybenzazole polymers, comprising an aromatic group, an o-amino-basic moiety bonded to the aromatic group, and an electron-deficient carbon group bonded to the aromatic group. The aromatic group, the electron-deficient carbon group and the o-amino-basic moiety have the definitions and preferred embodiments given herein. Examples of suitable AB-monomers and processes for their synthesis are provided in U.S. Pat. No. 4,533,693 at columns 33–35; Tables 7–8, which is incorporated herein by reference. Preferred examples of AB-monomers include 3-amino-4-hydroxybenzoic acid and 3-hydroxy-4-aminobenzoic acid. AB-monomers are frequently stored as salts of hydrogen chloride or phosphoric acid, because the free-base of the monomer is unstable and susceptible to air oxidation.

o-Amino-basic moiety—a moiety, which is bonded to an aromatic group, consisting essentially of
 (1) a primary amine group bonded to the aromatic group and
 (2) a hydroxy, thiol or primary or secondary amine group bonded to an aromatic carbon atom ortho to said primary amine group.

It preferably comprises a hydroxy, thiol or primary amine moiety, more preferably comprises a hydroxy or thiol moiety, and most preferably comprises a hydroxy moiety. o-Amino-basic moieties comprising hydroxy groups are o-amino-hydroxy moieties. Secondary amine groups comprise an aromatic or an aliphatic group and preferably an alkyl group. The secondary amine group preferably comprises no more than about 6 carbon atoms, more preferably no more than about 4 carbon atoms and most preferably no more than about 1 carbon atom.

Aromatic group (Ar)—any aromatic ring or ring system. Size is not critical as long as the aromatic group is not so big that it prevents further reactions of the moiety in which it is incorporated. Each aromatic group independently preferably comprises no more than about 18 carbon atoms, more preferably no more than about 12 carbon atoms and most preferably no more than about 6 carbon atoms. Each may be heterocyclic but is preferably carbocyclic and more preferably hydrocarbyl. If the aromatic group is heterocyclic, the heteroatom is preferably nitrogen.

Unless otherwise specified, each aromatic group may comprise a single aromatic ring, a fused ring system or an unfused ring system containing two or more aromatic moieties joined by bonds or by divalent moieties which are inert with respect to PBO polymerizing reagents under polymerization conditions. Suitable divalent moieties comprise, for example, a carbonyl group, a sulfonyl group, an oxygen atom, a sulfur atom, an alkyl group and/or and or a perfluorinated alkyl group. Each aromatic group is preferably a single six-membered ring.

Each aromatic group may contain substituents which are stable in solvent acid and do not interfere with further reactions of the moiety which the aromatic group is part of. Most preferably, each aromatic group contains only those substituents specifically called for hereinafter.

Azole ring—an oxazole, thiazole or imidazole ring. The carbon atom bonded to both the nitrogen atom and the oxygen, sulfur or second nitrogen atom is the 2-carbon, as depicted in Formula 3

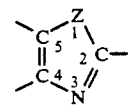

3 wherein Z is —O—, —S— or —NR—; and R is hydrogen, an aromatic or an aliphatic group, preferably hydrogen or an alkyl group, and most preferably hydrogen. R preferably comprises no more than about 6 carbon atoms, more preferably no more than about 4 and most preferably no more than about 1. Each azole ring is independently preferably oxazole or thiazole and more preferably oxazole. In PBO polymers, the 4- and 5-carbon of each azole ring is ordinarily fused with an aromatic group.

Azole-forming moiety—an "o-amino-hydroxy moiety" or "electron-deficient carbon group," as those terms are defined herein.

BB-Monomer—A monomer suitable for synthesizing polybenzazole polymers, comprising an aromatic group and two o-amino-basic moieties which are bonded to the aromatic group. The aromatic group and the o-amino-basic moieties have the definitions and preferred embodiments given herein. Examples of suitable BB-monomers and processes for synthesis are provided in U.S. Pat. No. 4,533,693 at columns 19–24, Tables 1–3, which is incorporated herein by reference. Examples of preferred BB-monomers include 4,6-diaminoresorcinol, 2,5-diaminohydroquinone and 1,4-dithio-2,5-diaminobenzene. BB-monomers are frequently stored as salts of hydrogen chloride or phosphoric acid, because the free base of the monomer is susceptible to air oxidation.

Electron-deficient carbon group (Q)—any group containing a carbon atom which can react in the solvent acid with an o-amino-basic moiety to form an azole ring, such as the groups listed in column 24, lines 59–66 of the U.S. Pat. No. 4,533,693, which is incorporated herein by reference. Preferred electron-deficient carbon groups are carboxylic acids, acid halides, metal carboxylate salts, cyano groups and trihalomethyl groups. Halogens in electron-deficient carbon groups are preferably chlorine, bromine or iodine and more preferably chlorine.

Polybenzazole (PBZ) polymer—A polymer from the group of polybenzoxazoles and polybenzobisoxazoles (PBO), polybenzothiazoles and polybenzobisthiazoles (PBT) and polybenzimidazoles or polybenzobisimidazoles (PBI). For the purposes of this application, the term "polybenzoxazole (PBO)" refers broadly to polymers in which each mer unit contains an oxazole ring bonded to an aromatic group, which need not necessarily be a benzene ring. The term "polybenzoxazole (PBO)" also refers broadly to poly(phenylene-benzobis-oxazole)s and other polymers wherein each mer unit comprises a plurality of oxazole rings fused to an aromatic group. The same understandings shall apply to the terms polybenzothiazole (PBT) and polybenzimidazole (PBI).

Rigid Rod PBO polymer - An "intrinsic" or "articulated" rigid rod PBO polymer as the terms "intrinsic" and "articulated" are defined in Hwang, "Processing, Structure and Properties of Liquid Crystalline PBT Polymer", Kansai Committee of the Society of Fiber Science and Technology, Japan, Post Symposium on Formation, Structure and Properties of High Modulus and High Tenacity Fibers 23–26 (August 26, 1985): Evers et al, "Articulated All-Para Polymers with 2,6-Benzobisoxazole, 2,6-Benobisthiazole, and 2,6-Benzobisimidazole Units in the Backbone," 14 Macromolecules 925 (1981): Evers, "Thermoxidatively Stable Articulated Benzobisoxazole and Benzobisthiazole Polymers," 24 J. Poly. Sci. Part A 1863 (1986) and Evers et al., *Articulated Para-Ordered Aromatic Heterocyclic Polymers Containing Diphenoxybenzene Structures*, U.S. Pat. No. 4,229,566 (Oct. 21, 1980).

Intrinsic rigid rod polymers are essentially rectilinear and have a persistence length comparable to their contour length. Articulated rigid rod polymers comprise a plurality of essentially rectilinear moieties joined by a relatively small number of non-linear moieties. Rigid rod PBO polymers used in the present invention are preferably intrinsic rigid rod polymers. If articulated, they preferably comprise on average no more than about 1 non-linear mer unit for each 9 essentially rectilinear mer units.

Solvent acid—any non-oxidizing liquid acid capable of dissolving PBO polymers, such as sulfuric acid, methanesulfonic acid, trifluoromethylsulfonic acid, polyphosphoric acid and mixtures thereof. It must be sufficiently non-oxidizing that it does not substantially oxidize AB- and BB-PBZ monomers which are dissolved therein. Solvent acids are preferably dehydrating acids, such as polyphosphoric acid or a mixture of methanesulfonic acid and phosphorus pentoxide. Polyphosphoric acid preferably has a $P_2O_5$ content by weight of at least about 75 percent, more preferably at least about 78 percent and preferably has a $P_2O_5$ content of at most about 90 percent, more preferably at most about 86 percent. The ratio of methanesulfonic acid to phosphorus pentoxide in mixtures of those compounds is preferably no more than about 20:1 by weight and no less than about 5 1 by weight.

DESCRIPTION OF THE INVENTION

One aspect of the present invention is a BB-PBO monomer having a pendant methyl group, comprising:
(1) an aromatic group:
(2) two o-amino-hydroxy moieties bonded to said aromatic group; and
(3) a methyl group bonded to said aromatic group.

The aromatic group and o-amino-hydroxy moieties have the meaning and preferred embodiments previously defined. The aromatic ring must be chosen such that it may be bonded to the five substituent groups described, i.e., it may be a pyridinyl moiety but not a pyrimidinyl moiety The aromatic group is highly preferably a six-membered ring and most preferably a phenylene moiety.

The o-amino-hydroxy moieties are preferably bonded to a six-membered aromatic group in para position with respect to each other, i.e., they are in the 1,6- and 3,4-positions on a phenylene ring or the 2,3- and 5,6-positions on a heterocyclic ring such as pyridine. The o-amino-hydroxy moieties are thus in cis- or trans-position as described in 11 Ency. Poly. Sci. & Eng., supra. at 602, which is incorporated herein by reference. The o-amino-hydroxy moieties are more preferably in cis-position, e.g., the amine groups are bonded to the 4- and 6-carbons and the hydroxy groups to the 1- and 3-carbons of the aromatic group on a phenylene moiety. Most preferably, the methyl group is bonded to the aromatic ring ortho to the two hydroxy groups (to the 2-carbon). (Of course, the numbering may be changed for substituents bonded to a heterocyclic aromatic group, but the preferred relative positions of those moieties should remain the same.) The aromatic group may have other substituents which do not interfere with the polymerization of the monomer or later reaction of the methyl group on the polymer, but it preferably does not have any other substituents.

The methyl-containing BB-monomer preferably conforms with formula 4(a)

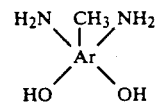

4(a)

more preferably conforms with 4(b)

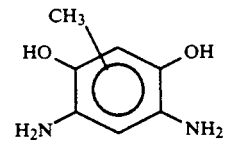

4(b)

and most preferably conforms to formula 4(c)

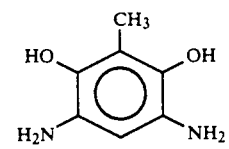

4(c).

wherein Ar is an aromatic group. The most preferred methyl-containing BB-monomer is 2-methyl-4,6-diaminoresorcinol.

The methyl-substituted BB-PBO monomer can be synthesized in a four-step process by:
(1) reacting an aromatic diol having a pendant methyl group, such as 2-methylresorcinol or 2-methylhydroquinone, with an alkyl haloformate under conditions such that a dicarbonate is formed:
(2) contacting the dicarbonate with nitric and sulfuric acids to nitrate it ortho to the ester moieties;
(3) converting the nitrated dicarbonate back to a nitrated diol, for instance by hydrolysis with lower alkanols in the presence of acids: and
(4) hydrogenating the nitro groups on the diol, such as catalytically or electrolytically. All four reactions are known individually in the art. The formation of dicarbonates is described in Meyers et al., 1978 *Tetrahedron Letters* 1375 (1978). Suitable nitration and reduction conditions are described in G. M. Loudon, *Organic Chemistry* 590, 596–610, and 1197 (Addison-Wesley Publ. Co. 1984): Lysenko, *High Purity Process for the Preparation of 4,6-Diamino-1,3-Benzenediol*, U.S. Pat. No. 4,766,244 (Aug. 23, 1988) and Gregory et al., *Electrochemical Synthesis of Substituted Aromatic Amines in Basic Media*, U.S. Pat. No. 4,764,263 (Aug. 16, 1988) which are incorporated by reference. The synthesis is more specifically described in U.S. patent application Ser. No. 290,068 (filed Dec. 27, 1988), which is incorporated herein by reference.

Monomers are typically stored as acid salts, such as hydrochloride salts or phosphate salts, to stabilize the monomer against air oxidation.

Methyl-containing BB-monomers are polymerized by a condensation reaction with AA-monomers, having the description and preferred embodiments previously given. Not all BB-monomers incorporated into the polymer must be methyl-containing BB-monomers of the present invention Methyl-containing BB-monomers preferably make up at least about 1 percent of all BB-monomers polymerized, more preferably at least about 5 percent, and most preferably at least about 10 percent. All BB-monomers may be methyl-containing BB-PBO monomers, but preferably no more than about 50 percent are. Suitable AA- and BB-monomers which may be polymerized with monomers of the present invention and conditions for synthesis are described in U.S. Pat. Nos. 4,533,692 and 4,533,693 and in Tsai et al., "Benzobisoxazole Rigid-rod Polymers with Pendant Methyl Groups," 29(2) ACS Polymer Preprints 324 (1988), which are incorporated herein by reference.

Some BB-monomers used to form polymers of the present invention may contain o-amino-thiol or o-diamino moieties, to form copolymers of PBO and PBT and/or PBI. Preferably, only monomers suitable to synthesize PBO are used.

The polymer that results from polymerization of methyl-containing BB-monomers is a polybenzazole polymer or copolymer having a plurality of mer units, wherein at least one mer unit comprises:
(a) a first aromatic group:
(b) two oxazole rings fused with the first aromatic group:
(c) a methyl group bonded to the first aromatic group: and
(d) a divalent organic moiety which is stable and inert under polybenzoxazole polymerizing conditions bonded to one of the azole rings. The aromatic group, oxazole rings and methyl group of the mer unit correspond to the aromatic group, o-amino-hydroxy moieties and the methyl group of the methyl-containing BB-monomer in a manner familiar to persons of ordinary skill in the art. The divalent organic moiety corresponds to the divalent organic moiety in AA-monomers used to synthesize the polymer.

Not all mer units need have pendant methyl groups. The proportions of mer units having pendent methyl groups are equivalent to the proportions of BB-monomer having methyl groups which are used to make the polymer. Mer units having pendant methyl groups preferably make up at least about 1 percent of the mer units in the polymer, more preferably at least about 5 percent and most preferably at least about 10 percent. All of the mer units may have pendant methyl groups, but preferably no more than about 50 percent do.

The polybenzazole polymer having pendant methyl groups may contain variations familiar to persons of ordinary skill in the art. For instance, the polymer may be end-capped using monofunctional reagents such as benzoic acid or o-aminophenol, as described in U.S. Pat. No. 4,703,103, which is incorporated herein by reference. AB-monomers may be used in the reaction mixture to synthesize copolymers containing both AB- and AA/BB-structures. Mixtures of different AA- and/or BB-monomers may be polymerized together to form copolymers of AA/BB-polybenzoxazole. Copolymers may be either random, sequential or block copolymers. Syntheses for making copolymers are described in detail in U.S. Pat. No. 4,533,693 columns 45–81, which is incorporated herein by reference. The methyl-containing mer units may be added to copolymers in blocks, but are preferably randomly or sequentially dispersed throughout the copolymer.

The polymer preferably contains at least about 15 mer units, more preferably at least about 50 mer units and most preferably at least about 100 mer units. When the polymer is a rigid rod polymer, it preferably has an inherent viscosity, as measured in methanesulfonic acid at 25° C. at about 0.05 g/dL concentration, of at least about 3 dL/g, more preferably at least about 10 dL/g, more highly preferably at least about 15 dL/g, and most preferably at least about 20 dL/g.

The polymer preferably comprises a moiety conforming to formula 5

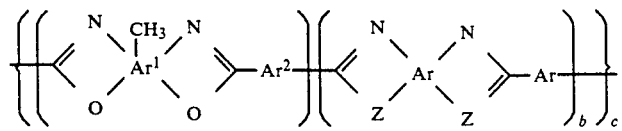

wherein
a is a number of repeating units equal to at least 1;
b is a number of repeating units 0 or greater;

c is a number of repeating units equal to at least one, a, b & c being chosen such that the polymer comprises a plurality of mer units; and all other characters have the meanings previously given.

The polybenzazole polymer is synthesized in a dope solution with a solvent acid. The polymer is coagulated from acid dopes to form shaped articles such as fibers, films or powders by known techniques, as described in 11 Ency. Poly. Sci. & Eng., supra. at 625–28: U.S. Pat. No. 4,533,693 at columns 82–84; Hwang et al., "Solution Processing and Properties of Molecular Composite Fibers and Films," 23 Poly. Eng. & Sci. 784, 785 (1984): and Hwang et al., "Composites on a Molecular Level: Phase Relationships, Processing, and Properties," B22(2) J. Macromol. Sci--Phys. 231, 234–35 (1983), which are incorporated herein by reference. Films and fibers can be used in composites and laminates as described in 11 Ency. Poly. Sci. & Eng., supra, at 625–30, which is incorporated herein by reference.

The pendent methyl groups on a polymer may be oxidized by contact with an oxidizing agent in a solvent acid to form an equivalent polymer having pendant carboxylic acid groups in the place of the methyl groups. The oxidation of benzylic alkyl groups to carboxylic acid groups is known and reported in standard chemical texts, such as B. S. Furniss et al., *Vogel's Textbook of Practical Organic Chemistry* 819 (Longman House 1978) and G. M. Loudon, *Organic Chemistry* 618 (Addison-Wesley Publ. Co. 1984), which are incorporated herein by reference.

The coagulated polymer can be cross-linked by heat treatment at a temperature and for a time sufficient for cross-linking to occur. The cross-linking reaction is preferably carried out in the presence of air. The temperature is preferably at least 150° C., more preferably at least 200° C., and most preferably at least 250° C. The temperature is preferably at most 700° C., and more preferably at most 600° C. The optimal residence time for cross-linking varies depending upon the temperature of heat treatment, the concentration od cross-linking sites and the desired degree of cross-linking in a manner familiar to persons of ordinary skill in the art. At higher temperatures, cross-linking occurs at a faster rate, and it may be desirable to shorten residence time in order to minimize thermal degradation of the polymer. For instance, about one minute or less may be sufficient at 600° C. On the other hand, the residence time for heat treatment at 250° C. is preferably at least about 1 hour, more preferably at least about 2 hours, more highly preferably at least about 3 hours and most preferably at least about 4 hours.

The cross-linked polymer contains polymer chains having the description previously given, which are linked by cross-linking moieties, which contain methylene moieties bonded to aromatic groups, which are fused with two azole rings in the polymer backbone. One of the aromatic groups bonded to the methylene moiety must correspond to the aromatic group which was bonded to the methyl group before cross-linking, i.e., it must be fused with two azole rings. The cross-linked polymers have a higher resistance to dissolution, swelling and loss of shape in traditional solvent acids, as compared with uncross-linked polymers.

WORKING EXAMPLES

The following examples are for illustrative purposes only and should not be interpreted as limiting the scope of either the specification or the claims. Unless stated otherwise, all parts and percentages are given by weight.

EXAMPLE 1

Synthesis of 2-methyl-4,6-diaminoresorcinol dihydrochloride

2-Methyl-4,6-diaminoresorcinol dihydrochloride is synthesized by the following procedure:

(A) a mixture of 310 g of 2-methylresorcinol, 1.5 L of methylene chloride, 625 g of 50 percent sodium hydroxide and 800 ml of deionized water is cooled to about 0° C. with stirring. A 500-ml quantity of methyl chloroformate is added dropwise at a rate sufficient to maintain the temperature of the reaction between 8° C. and 15° C. A mixture of 250 g of 50 percent sodium hydroxide, 250 g of deionized water and 20 ml of triethylamine is added. An additional 125 ml of methyl chloroformate is added and the mixture is heated to 25° C. and stirred for 45 minutes. A 1000-ml quantity of deionized water is added, and mixing is continued for about 15 minutes. The mixture is separated into two layers, and the organic layer is recovered.

(B) The organic phase from Part (A) is cooled to 0° C., and 2860 g of concentrated sulfuric acid is added with stirring. A 495.1-g quantity of concentrated nitric acid is added at a rate sufficient to maintain the reaction temperature between 10° C. and 20° C. When the addition is complete, the reaction mixture is heated to 40° C., and stirring is continued for 5 hours. The mixture is cooled to 10° C., and 1500 ml of deionized water is added at a rate sufficient to maintain the reaction temperature below 25° C. The reaction mixture is allowed to separate into layers, and the organic layer is recovered. The organic solvent is drawn off under vacuum. The recovered nitration product is a tacky yellow substance weighing 883 g when wet.

(C) A 441-g quantity of the wet product of Part (B) (approximately ½) is dissolved in 500 ml of methanol. The mixture is cooled to 15° C. while 1200 ml of deionized water is added. A mixture of 700 g of 50 percent sodium hydroxide and 300 g of deionized water is added. After stirring for 1 hour at 25° C., the temperature is increased to 44° C., and 25 g of 50 percent sodium hydroxide is added. The mixture is heated at 56° C. for 2 hours, then cooled to 10° C. A 1000-ml quantity of concentrated hydrochloric acid is added dropwise, allowing each drop to disperse before adding the next drop. The resulting yellow precipitate is filtered and washed with water. It has a weight of 310 g wet. The procedure is repeated with the other half of the product from step (B), to yield 302 g of wet cake.

(D) A 310-g quantity of 2-methyl-4,6-dinitro-resorcinol from Part (C) is dissolved in 3 L of 1 propanol in a reactor. The reactor is purged with nitrogen for 5 minutes. A 15-g quantity of slurry containing by weight one-half 10 percent palladium-on-carbon and one-half water is added with 80 g of deionized water. The reactor is purged with nitrogen again. Hydrogen is bubbled through the mixture at a temperature between 45° C. and 55° C. until hydrogen uptake ceases. The mixture is cooled to 30° C., and 30 g of tin(II) dichloride dihydrate dissolved in 1 L of concentrated HCl is added. The resulting precipitate is filtered. A mixture containing 360 g of precipitate, 1.5 L of concentrated HCl, 50 g of tin(II) dichloride dihydrate and 1.3 L of deionized water is heated to reflux and filtered. The filtrate is heated, and 50 g of Calgon PWA ™ activated carbon is added. The mixture is refluxed and filtered. A mixture of 5 g tin(II) dichloride dihydrate and 300 ml of hydrochloric acid is added. The mixture is cooled and filtered. The filtrate is vacuum dried to leave 277 g of 2-methyl-4,6-diaminoresorcinol dihydrochloride as a fine white crystalline cake.

EXAMPLE 2

Synthesis of homopolymer of 2-methyl-4,6-diaminoresorcinol dihydrochloride and terephthaloyl chloride The amounts of 2-methyl-4,6-diaminoresorcinol dihydrochloride (DAR), terephthaloyl chloride (TC) and polyphosphoric acid (PPA) having a $P_2O_5$ content between 76.2 and 77 percent, as shown in Table I, are mixed under nitrogen atmosphere. The mixture is heated with agitation under nitrogen atmosphere for 16 hours at $T^1$ and 24 hours at $T^2$. The temperature of the mixture is raised to $T^3$, and the amount of $P_2O_5$ shown is added. The mixture is heated for 24 hours each at $T^3$, $T^4$ and $T^5$ with continued agitation under nitrogen atmosphere. A sample of the polymer is coagulated in water, washed, ground, rewashed, dried and dissolved in methanesulfonic acid. It has the inherent viscosity shown in Table I, at a temperature of 25° C. and a concentration of about 0.05 g/dL.

TABLE I

| Sample | MDAR (g) | TC (g) | PPA (g) | $T^1$ (°C.) | $T^2$ (°C.) | $P_2O_5$ (g) | $T^3$ (°C.) | $T^4$ (°C.) | $T^5$ (°C.) | I.V. (dL/g) |
|---|---|---|---|---|---|---|---|---|---|---|
| 1 | 6.80 | 6.08 | 29.9 | 40 | 50 | 15.9 | 95 | 135 | 190 | 17.6 |
| 2 | 10.0 | 8.94 |  | 35 | 45 | 22.8 | 95 | 150 | 190 | 19.8 |
| 3 | 10.00* | 8.94 | 41.2 | 45* | 45 | 24.2 | 95 | 150 | 190 | 10.6 |
| 4 | 10.00 | 8.94 | 41.2 | 25 | 40 | 24.2 | 95 | 150 | 190 | 19.3 |

*MDAR is not added until after heating for 16 hours at $T^1$

EXAMPLE 3

Synthesis of copolymer containing pendant methyl groups

Under nitrogen atmosphere, 1.71 g (7.51 mmoles) of 2-methyl-4,6-diaminoresorcinol dihydrochloride, 8.00 g (37.6 mmoles) of 4,6-diaminoresorcinol dihydrochloride, 9.15 g (45.1 mmoles) of terephthaloyl chloride, and 40.2 g of polyphosphoric acid (containing 76.4 percent $P_2O_5$) are agitated. The mixture is heated for 16 hours at 40° C. and 24 hours at 50° C. The temperature is raised to 95° C., and 23.5 g of $P_2O_5$ is added. The reaction is continued for 24 hours each at 95° C., 150° C. and 190° C. The inherent viscosity is measured as described in Example 2 at 15.9 dL/g.

EXAMPLE 4

Synthesis of copolymer containing pendant methyl groups

Under nitrogen atmosphere, 5.32 g (23.5 mmoles) of 2-methyl-4,6-diaminoresorcinol dihydrochloride, 5.00 g (23.5 mmoles) of 4,6-diaminoresorcinol dihydrochloride, 9.53 g (46.9 mmoles) of terephthaloyl chloride and 42.2 g of polyphosphoric acid (76.0 weight percent $P_2O_5$) are agitated. The mixture is heated for 16 hours at 45° C. The temperature is raised to 95° C., and 25.6 g of $P_2O_5$ is added. The reaction is continued for 8 hours at 95° C., 16 hours at 150° C. and 24 hours at 190° C. The resulting polymer has an inherent viscosity, determined as in Example 2, of 19.6 dL/g.

EXAMPLE 5

Synthesis of cross-linked methyl-PBO

A methyl-cis-PBO homopolymer synthesized as described in Example 2 is dissolved in methanesulfonic acid to form a 1.5 weight percent solution. The solution is cast onto glass and then coagulated with water. The cast film is washed with aqueous sodium hydroxide, dried and cut into strips. The strips are heated in air at 250° C. for varying times and then placed in methanesulfonic acid. The untreated film dissolves completely in 15 minutes. The film treated for one hour leaves some undissolved swollen material after 8 hours, but is completely dissolved after 24 hours. The film treated for 2 hours swells and loses shape but does not dissolve after 24 hours. The film treated for 3 hours swells after 24 hours but retains its shape. The film treated for 4 hours, 6 hours and 24 hours swells only slightly or not at all.

EXAMPLE 6

Synthesis of methyl-cis-PBO-copolymer and fiber spun from it

The process of Example 4 is repeated. Fibers are spun as described in U.S. Pat. No. 4,533,693. The fibers have a tensile strength of 432,000 psi and a tensile modulus of 35,400,000 psi and an elongation to break of 1.7 percent. Heat-treated fiber does not dissolve in methanesulfonic acid. Unheat-treated fiber has an inherent viscosity of 19.6 dL/g when measured as in Example 2.

What is claimed is:

1. A monomer suitable for synthesizing polybenzoxazole polymers, said monomer comprising:
   (a) an aromatic group;
   (b) two o-amino-hydroxy moieties bonded to the aromatic group; and
   (c) a methyl group bonded to the aromatic group.

2. The monomer of claim 1 wherein the aromatic group is a pentavalent phenylene or pyridinyl moiety.

3. The monomer of claim 2 wherein the o-amino-hydroxy moieties are in the 1,6- and 3,4-positions on a phenylene ring or the 2,3- and 5,6-positions on a pyridine ring.

4. The monomer of claim 3 wherein the hydroxy and amine groups of the o-amino-hydroxy groups are in cis-position with respect to each other.

5. The monomer of claim 4 wherein the aromatic group is a pentavalent phenylene moiety.

6. The monomer of claim 5 wherein the monomer is 2-methyl-4,6-diaminoresorcinol or an acid salt thereof.

* * * * *